US010106887B2

(12) United States Patent
Lansalot-Matras et al.

(10) Patent No.: US 10,106,887 B2
(45) Date of Patent: Oct. 23, 2018

(54) GROUP 5 TRANSITION METAL-CONTAINING COMPOUNDS FOR VAPOR DEPOSITION OF GROUP 5 TRANSITION METAL-CONTAINING FILMS (71) Applicants: L'AIR LIQUIDE, SOCIETE ANONYME POUR L'ETUDE ET L'EXPLOITATION DES PROCEDES GEORGES CLAUDE, Paris (FR); Clement Lansalot-Matras, Seocho-gu, Seoul (KR); Wontae Noh, Jung-gu, Seoul (KR); Jooho Lee, Gajaeul-ro, Seodaemun-gu, Seoul (KR)

(72) Inventors: Clément Lansalot-Matras, Princeton, NJ (US); Wontae Noh, Seoul (KR); Jooho Lee, Seoul (KR)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 0 days.

(21) Appl. No.: 15/035,592

(22) PCT Filed: Nov. 13, 2013

(86) PCT No.: PCT/KR2013/010274
§ 371 (c)(1),
(2) Date: May 10, 2016

(87) PCT Pub. No.: WO2015/072589
PCT Pub. Date: May 21, 2015

(65) Prior Publication Data
US 2016/0251756 A1 Sep. 1, 2016

(51) Int. Cl.
C23C 16/18 (2006.01)
C23C 16/455 (2006.01)
C01G 33/00 (2006.01)
C07F 9/00 (2006.01)
C09D 5/24 (2006.01)
H01L 21/02 (2006.01)
H01L 21/285 (2006.01)
C23C 16/452 (2006.01)

(52) U.S. Cl.
CPC ............ C23C 16/18 (2013.01); C01G 33/00 (2013.01); C07F 9/005 (2013.01); C09D 5/24 (2013.01); C23C 16/45536 (2013.01); C23C 16/45553 (2013.01); H01L 21/0228 (2013.01); H01L 21/02175 (2013.01); H01L 21/02208 (2013.01); H01L 21/02271 (2013.01); H01L 21/28556 (2013.01); H01L 21/28568 (2013.01); C01P 2006/40 (2013.01); C23C 16/452 (2013.01)

(58) Field of Classification Search
CPC ........ C23C 16/18; C01G 31/00; C01G 33/00; C01G 35/00
See application file for complete search history.

(56) References Cited

U.S. PATENT DOCUMENTS

| 7,837,797 | B2* | 11/2010 | Derderian | ............. C23C 16/405 118/715 |
| 2003/0224600 | A1* | 12/2003 | Cao | ........................ C23C 16/045 438/684 |
| 2004/0187778 | A1* | 9/2004 | Gros-Jean | ............. C23C 16/405 118/715 |
| 2008/0004858 | A1 | 1/2008 | Gao et al. | |
| 2008/0141937 | A1* | 6/2008 | Clark | ...................... C23C 16/16 118/697 |
| 2008/0241575 | A1 | 10/2008 | Lavoie et al. | |
| 2010/0055310 | A1 | 3/2010 | Merle et al. | |
| 2012/0127629 | A1 | 5/2012 | Roeder et al. | |

FOREIGN PATENT DOCUMENTS

| EP | 2 065 390 | 6/2009 |
| JP | 2003 335740 | 11/2003 |
| WO | WO 2007 141059 | 12/2007 |

OTHER PUBLICATIONS

F. Preuss et al. Amido-rm-butylimidovanadium(V) Compounds. Synthesis, Reactions and 51V NMR Spectroscopic Studies. Z. Naturforsch. 56 b, 1100-1108 (2001); eingegangen am Jun. 27, 2001. English Abstract.*
Amemiya, K. et al., "High energy aluminum ion implantation using a variable energy radio frequency quadrupole implanter," J. Vac. Sci. Technol. A 16(2), Mar./Apr. 1998, 472-476.
Blanquart, T. et al., "Evaluation and comparison of novel precursors for atomic layer deposition of $Nb_2O_5$ thoin films," Chem. Mater. 2012, 24, 975-980.
Chiu, H.-T. et al., "Metal-organic CVD of tantalum oxide from tert-butylimidotris (diethylamido)tantalum and oxygen," Chem. Vap. Deposition, 2000, 6(5), 223-225.
Felch, S.B. et al., "Plasma doping for the fabrication of ultra-shallow junctions," Surface and Coatings Technology 156 (2002) 229-236.
Forsgren, K. et al., "Halide chemical vapour deposition of $Ta_2O_5$," Thin Solid Films 343-344 (1999) 111-114.
Knapas, K. et al., "Etching of $Nb_2O_5$ thin films by $NbCl_5$," Chem. Vap. Deposition 2009, 15, 269-273.
Knapas, K. et al., "Reaction mechanism studies on atomic layer deposition of $Nb_2O_5$ from $Nb(OEt)_5$ and water," Langmuir 2010, 26(2), 848-853.
Kukli, K. et al., "Niobium oxide thin films grown by atomic layer epitaxy," Chem. Vap. Deposition 1998, 4(1), 29-34.
Lintanf-Salaën, A. et al., "Atomic layer deposition of tantalum oxide thin films for their use as diffusion barriers in microelectronic devices," Microelectronic Engineering 87 (2010) 373-378.
Preuss, F. et al., "Phosphan-, phosphit- und phosphido-komplexe des Vanadiums(V)" with English abstract, Zeitschrift für Anorganische und Allgemeine Chemie, vol. 623, issue 8, Aug. 1997, 1220-1228.

(Continued)

Primary Examiner — David P Turocy
(74) Attorney, Agent, or Firm — Patricia E. McQueeney (57) ABSTRACT Disclosed are Group 5 transition metal-containing thin film forming precursors. Also disclosed are methods of synthesizing and using the disclosed precursors to deposit Group 5 transition metal-containing thin films on one or more substrates via vapor deposition processes.

12 Claims, 4 Drawing Sheets (56) References Cited

OTHER PUBLICATIONS

Song, M.-K. et al., "Formation of tantalum carbide and nitride phases in atomic layer deposition using hydrogen plasma and tert-butylimido-tris(diethylamido)-tantalum (TBTDET), and its effect on material properties," Chem. Vap. Deposition, 2008, 14, 334-338.
Yotsuya, T. et al., "Novel highly volatile MOCVD precursors for $Ta_2O_5$ and $Nb_2O_5$ thin films," ECS Transactions, 16(5) 243-251 (2008).
International Search Report and Written Opinion for corresponding PCT/KR2013/010274, dated Aug. 5, 2014.

\* cited by examiner

GROUP 5 TRANSITION METAL-CONTAINING COMPOUNDS FOR VAPOR DEPOSITION OF GROUP 5 TRANSITION METAL-CONTAINING FILMS

CROSS REFERENCE TO RELATED APPLICATIONS

This application is a 371 of International PCT Application PCT/KR2013/010274, filed Nov. 13, 2013, the entire contents of which are incorporated herein by reference.

TECHNICAL FIELD

Disclosed are Group 5 transition metal-containing thin film forming precursors. Also disclosed are methods of synthesizing and using the disclosed precursors to deposit Group 5 transition metal-containing films on one or more substrates via vapor deposition processes.

BACKGROUND

In the research of semiconductor coatings, memories, and displays, the precursor molecule plays an important role to obtain high quality thin films. It controls many parameters such as conformality and affects physical and electrical properties of thin films. The precursor molecules require high purity, high thermal stability, high volatility, appropriate reactivity, and low toxicity. Additionally, in processes of thin films, the precursor molecules should vaporize in a limited time and at a reproducible rate for Chemical Vapor Deposition (CVD) or Atomic Layer Deposition (ALD).

In semiconductor areas, Group 5 transition metal-containing films have long been utilized for a variety of applications. The resistance switching characteristics of $M_xO_y$ thin films show its potential applications for the next generation nonvolatile resistive random access memory (ReRAM) devices as well as for high-k capacitor applications such as a thin layer in-between $ZrO_2$ layers to reduce leak current and stabilize the phase.

Typical Group 5 transition metal halides have been explored for the deposition of $M_xO_y$ (M=Nb, Ta; x=1-2; y=1-5) by CVD or ALD. Those precursors, mainly $NbCl_5$ or $TaCl_5$, may require high deposition temperatures and are sometimes not appropriate as precursors due to etching effects and precursor residues. Chem. Vap. Deposition 2009, 15, 269-273; Thin Solid Films, 1999, 111).

$Nb(OEt)_5$ has shown promising results to deposit amorphous $Nb_2O_5$ by ALD with a stable temperature windows of 230-260° C.) (Chem. Vap. Deposition 1998, 4, pp. 29-34). In addition, the precursor has been used to study the mechanism of $Nb_xO_y$ ALD depositions using $H_2O$ or $D_2O$ (Langmuir 2010, 26(2), pp. 848-853).

In case of $Ta(OEt)_5$, ALD of $Ta_2O_5$ with $H_2O$ has shown a process window between 170° C. and 230° C., having amorphous phase at 600° C., as deposited and crystalline phase at 800° C. (Microelec. Eng. 2010, 87, pp. 373-378).

Imido-type precursors are known and used to deposit Group 5 transition metal containing films. They are mostly in a liquid phase with high vapor pressure, which provide an advantage for vaporizing and transferring to a reaction chamber. Many derivatives have been studied for CVD (Chem. Vap. Deposition 2008, 14, pp. 334-338; Chem. Vap. Deposition 2000, 6, pp. 223-225; ECS Trans. 2008, 16 (5), pp. 243-251) or ALD (Chem. Mater. 2012, 24, pp. 975-980). However, those precursors showed limited ALD temperature windows with a maximum of 275° C.

Other similar structures with mixed ligands of Group 5 transition metal have been described, such as V(=NtBu)(NiPr$_2$)(OtBu)$_2$. Zeitschrift fuer Anorganische and Allgemeine Chemie (1997) 623 (8), pp. 1220-1228, but have not considered for thin film applications.

A need remains for novel group 5 transition metal-containing compounds suitable for vapor phase thin film deposition.

SUMMARY

Disclosed are Group 5 transition metal-containing compounds having one of the following formulae:

Formula I

Formula II wherein M is selected from Group 5 transition metals consisting of V, Nb, or Ta and each $R^1$, $R^2$, $R^3$, $R^5$, and $R^6$ is independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. In Formula I, $R^3$ and $R^4$ may be identical or different. In Formula II, $R^4$ and $R^5$ may be identical or different. In Formula I, $R^3$, $R^4$, $R^5$ and $R^6$ may be identical or different.

The disclosed Group 5 transition metal-containing compounds may further include one or more of the following aspects:

- M being V;
- M being Nb;
- M being Ta;
- $R^1$ being tBu or tert-amyl;
- $R^2$ in Formula I being iPr or tBu;
- $R^2$ and $R^3$ in Formula II being iPr or tBu;
- $R^3$, $R^4$, $R^5$, and $R^6$ in Formula I being Me or Et;
- $R^4$ and $R^5$ in Formula II being Me or Et;
- the Group 5 transition metal-containing compound being tert-butylimidobis(diethylamido)mono(iso-propylalkoxo)Vanadium(V);
- the Group 5 transition metal-containing compound being tert-butylimidobis(diethylamido)mono(tert-butylalkoxo)Vanadium (V);
- the Group 5 transition metal-containing compound being tert-butylimidobis(dimethylamido)mono(iso-propylalkoxo)Vanadium (V);
- the Group 5 transition metal-containing compound being tert-butylimidobis(dimethylamido)mono(tert-butylalkoxo)Vanadium (V);
- the Group 5 transition metal-containing compound being tert-amylimidobis(diethylamido)mono(iso-propylalkoxo)Vanadium (V);

the Group 5 transition metal-containing compound being tert-amylimidobis(diethylamido)mono(tert-butylalkoxo)Vanadium (V);

the Group 5 transition metal-containing compound being tert-amylimidobis(dimethylamido)mono(iso-propylalkoxo)Vanadium (V);

the Group 5 transition metal-containing compound being tert-amylimidobis(dimethylamido)mono(tert-butylalkoxo)Vanadium (V);

the Group 5 transition metal-containing compound being tert-butylimidobis(tertbutylamido)mono(tert-butylalkoxo)Vanadium(V);

the Group 5 transition metal-containing compound being tert-butylimidobis(di(trimethylsilyl)amido)mono(tert-butylalkoxo)Vandadium(V);

the Group 5 transition metal-containing compound being tert-butylimidobis(dimethylamido)mono(diethylhydroxylamino)Vanadium(V);

the Group 5 transition metal-containing compound being tert-butylimidobis(diethylamido)mono(iso-propylalkoxo)Niobium(V);

the Group 5 transition metal-containing compound being tert-butylimidobis(diethylamido)mono(tert-butylalkoxo)Niobium(V);

the Group 5 transition metal-containing compound being tert-butylimidobis(dimethylamido)mono(iso-propylalkoxo)Niobium(V);

the Group 5 transition metal-containing compound being tert-butylimidobis(dimethylamido)mono(tert-butylalkoxo)Niobium(V);

the Group 5 transition metal-containing compound being tert-amylimidobis(diethylamido)mono(iso-propylalkoxo)Niobium(V);

the Group 5 transition metal-containing compound being tert-amylimidobis(diethylamido)mono(tert-butylalkoxo)Niobium(V);

the Group 5 transition metal-containing compound being tert-amylimidobis(dimethylamido)mono(iso-propylalkoxo)Niobium(V);

the Group 5 transition metal-containing compound being tert-amylimidobis(dimethylamido)mono(tert-butylalkoxo)Niobium(V);

the Group 5 transition metal-containing compound being tert-butylimidobis(tertbutylamido)mono(tert-butylalkoxo)Niobium(V);

the Group 5 transition metal-containing compound being tert-butylimidobis(di(trimethylsilyl)amido)mono(tert-butylalkoxo)Niobium(V);

the Group 5 transition metal-containing compound being tert-butylimidobis(dimethylamido)mono(diethylhydroxylamino)Niobium(V);

the Group 5 transition metal-containing compound being tert-butylimidobis(diethylamido)mono(iso-propylalkoxo)Tantalum(V);

the Group 5 transition metal-containing compound being tert-butylimidobis(diethylamido)mono(tert-butylalkoxo) Tantalum (V);

the Group 5 transition metal-containing compound being tert-butylimidobis(dimethylamido)mono(iso-propylalkoxo)Tantalum(V);

the Group 5 transition metal-containing compound being tert-butylimidobis(dimethylamido)mono(tert-butylalkoxo)Tantalum (V);

the Group 5 transition metal-containing compound being tert-amylimidobis(diethylamido)mono(iso-propylalkoxo)Tantalum (V);

the Group 5 transition metal-containing compound being tert-amylimidobis(diethylamido)mono(tert-butylalkoxo)Tantalum (V);

the Group 5 transition metal-containing compound being tert-amylimidobis(dimethylamido)mono(iso-propylalkoxo)Tantalum (V);

the Group 5 transition metal-containing compound being tert-amylimidobis(dimethylamido)mono(tert-butylalkoxo)Tantalum (V);

the Group 5 transition metal-containing compound being tert-butylimidobis(tertbutylamido)mono(tert-butylalkoxo)Tantalum(V);

the Group 5 transition metal-containing compound being tert-butylimidobis(di(trimethylsilyl)amido)mono(tert-butylalkoxo)Tantalum(V);

the Group 5 transition metal-containing compound being tert-butylimidobis(dimethylamido)mono(diethylhydroxylamino)Tantalum(V);

the Group 5 transition metal-containing compound being tert-butylimidomono(diethylamido)bis(iso-propylalkoxo)Vanadium(V);

the Group 5 transition metal-containing compound being tert-butylimidomono(diethylamido)bis(tert-butylalkoxo)Vanadium (V);

the Group 5 transition metal-containing compound being tert-butylimidomono(dimethylamido)bis(iso-propylalkoxo) Vanadium (V);

the Group 5 transition metal-containing compound being tert-butylimidomono(dimethylamido)bis(tert-butylalkoxo) Vanadium (V);

the Group 5 transition metal-containing compound being tert-amylimidomono(diethylamido)bis(iso-propylalkoxo) Vanadium (V);

the Group 5 transition metal-containing compound being tert-amylimidomono(diethylamido)bis(tert-butylalkoxo) Vanadium (V);

the Group 5 transition metal-containing compound being tert-amylimidomono(dimethylamido)bis(iso-propylalkoxo) Vanadium (V);

the Group 5 transition metal-containing compound being tert-amylimidomono(dimethylamido)bis(tert-butylalkoxo) Vanadium (V);

the Group 5 transition metal-containing compound being tert-butylimidomono(tert-butylamido)bis(tert-butylalkoxo)Vanadium(V);

the Group 5 transition metal-containing compound being tert-butylimidomono(di(trimethylsilyl)amido)bis(tert-butylalkoxo)Vanadium(V);

the Group 5 transition metal-containing compound being tert-butylimidomono(dimethylamido)bis(diethylhydroxylamino)Vanadium(V);

the Group 5 transition metal-containing compound being tert-butylimidomono(diethylamido)bis(iso-propylalkoxo)Niobium(V);

the Group 5 transition metal-containing compound being tert-butylimidomono(diethylamido)bis(tert-butylalkoxo) Niobium(V);

the Group 5 transition metal-containing compound being tert-butylimidomono(dimethylamido)bis(iso-propylalkoxo)Niobium(V);

the Group 5 transition metal-containing compound being tert-butylimidomono(dimethylamido)bis(tert-butylalkoxo)Niobium(V);

the Group 5 transition metal-containing compound being tert-amylimidomono(diethylamido)bis(iso-propylalkoxo)Niobium(V);

the Group 5 transition metal-containing compound being tert-amylimidomono(diethylamido)bis(tert-butylalkoxo)Niobium(V);

the Group 5 transition metal-containing compound being tert-amylimidomono(dimethylamido)bis(iso-propylalkoxo)Niobium(V);

the Group 5 transition metal-containing compound being tert-amylimidomono(dimethylamido)bis(tert-butylalkoxo)Niobium(V);

the Group 5 transition metal-containing compound being tert-butylimidomono(tert-butylamido)bis(tert-butylalkoxo)Niobium(V);

the Group 5 transition metal-containing compound being tert-butylimidomono(di(trimethylsilyl)amido)bis(tert-butylalkoxo)Niobium(V);

the Group 5 transition metal-containing compound being tert-butylimidomono(dimethylamido)bis(diethylhydroxylamino)Niobium(V);

the Group 5 transition metal-containing compound being tert-butylimidomono(diethylamido)bis(iso-propylalkoxo)Tantalum(V);

the Group 5 transition metal-containing compound being tert-butylimidomono(diethylamido)bis(tert-butylalkoxo)Tantalum(V);

the Group 5 transition metal-containing compound being tert-butylimidomono(dimethylamido)bis(iso-propylalkoxo)Tantalum(V);

the Group 5 transition metal-containing compound being tert-butylimidomono(dimethylamido)bis(tert-butylalkoxo)Tantalum(V);

the Group 5 transition metal-containing compound being tert-amylimidomono(diethylamido)bis(iso-propylalkoxo)Tantalum(V);

the Group 5 transition metal-containing compound being tert-amylimidomono(diethylamido)bis(tert-butylalkoxo)Tantalum(V);

the Group 5 transition metal-containing compound being tert-amylimidomono(dimethylamido)bis(iso-propylalkoxo)Tantalum(V);

the Group 5 transition metal-containing compound being tert-amylimidomono(dimethylamido)bis(tert-butylalkoxo)Tantalum(V);

the Group 5 transition metal-containing compound being tert-butylimidomono(tert-butylamido)bis(tert-butylalkoxo)Tantalum(V);

the Group 5 transition metal-containing compound being tert-butylimidomono(di(trimethylsillyl)amido)bis(tert-butylalkoxo)Tantalum(V); and the Group 5 transition metal-containing compound being tert-butylimidomono(dimethylamido)bis(diethylhydroxylamino)Tantalum(V).

Also disclosed are Group 5 transition metal-containing thin film forming precursors having one of the following formulae:

Formula I

Formula II wherein M is selected from Group 5 transition metals consisting of V, Nb, or Ta and each $R^1$, $R^2$, $R^3$, $R^4$, $R^5$, and $R^6$ is independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. In Formula I, $R^3$ and $R^4$ may be identical or different. In Formula II, $R^4$ and $R^5$ may be identical or different. In Formula I, $R^3$, $R^4$, $R^5$ and $R^6$ may be identical or different.

The disclosed Group 5 transition metal-containing thin film forming precursors may further include one or more of the following aspects:

M being V;

M being Nb;

M being Ta;

$R^1$ being tBu or tert-amyl;

$R^2$ in Formula I being iPr or tBu;

$R^2$ and $R^3$ in Formula II being iPr or tBu;

$R^3$, $R^4$, $R^5$, and $R^6$ in Formula I being Me or Et;

$R^4$ and $R^5$ in Formula II being Me or Et;

the Group 5 transition metal-containing thin film forming precursor being tert-butylimidobis(diethylamido)mono(iso-propylalkoxo)Vanadium(V);

the Group 5 transition metal-containing thin film forming precursor being tert-butylimidobis(diethylamido)mono(tert-butylalkoxo)Vanadium (V);

the Group 5 transition metal-containing thin film forming precursor being tert-butylimidobis(dimethylamido)mono(iso-propylalkoxo)Vanadium (V);

the Group 5 transition metal-containing thin film forming precursor being tert-butylimidobis(dimethylamido)mono(tert-butylalkoxo)Vanadium (V);

the Group 5 transition metal-containing thin film forming precursor being tert-amylimidobis(diethylamido)mono(iso-propylalkoxo)Vanadium (V);

the Group 5 transition metal-containing thin film forming precursor being tert-amylimidobis(diethylamido)mono(tert-butylalkoxo)Vanadium (V);

the Group 5 transition metal-containing thin film forming precursor being tert-amylimidobis(dimethylamido)mono(iso-propylalkoxo)Vanadium (V);

the Group 5 transition metal-containing thin film forming precursor being tert-amylimidobis(dimethylamido)mono(tert-butylalkoxo)Vanadium (V);

the Group 5 transition metal-containing thin film forming precursor being tert-butylimidobis(tertbutylamido)mono(tert-butylalkoxo)Vanadium(V);

the Group 5 transition metal-containing thin film forming precursor being tert-butylimidobis(di(trimethylsilyl)amido)mono(tert-butylalkoxo)Vandadium(V);

the Group 5 transition metal-containing thin film forming precursor being tert-butylimidobis(dimethylamido)mono(diethylhydroxylamino)Vanadium(V);

the Group 5 transition metal-containing thin film forming precursor being tert-butylimidobis(diethylamido)mono(iso-propylalkoxo)Niobium(V);

the Group 5 transition metal-containing thin film forming precursor being tert-butylimidobis(diethylamido)mono(tert-butylalkoxo)Niobium(V);

the Group 5 transition metal-containing thin film forming precursor being tert-butylimidobis(dimethylamido)mono(iso-propylalkoxo)Niobium(V);

the Group 5 transition metal-containing thin film forming precursor being tert-butylimidobis(dimethylamido)mono(tert-butylalkoxo)Niobium(V);

the Group 5 transition metal-containing thin film forming precursor being tert-amylimidobis(diethylamido)mono(iso-propylalkoxo)Niobium(V);

the Group 5 transition metal-containing thin film forming precursor being tert-amylimidobis(diethylamido)mono(tert-butylalkoxo)Niobium(V);

the Group 5 transition metal-containing thin film forming precursor being tert-amylimidobis(dimethylamido)mono(iso-propylalkoxo)Niobium(V);

the Group 5 transition metal-containing thin film forming precursor being tert-amylimidobis(dimethylamido)mono(tert-butylalkoxo)Niobium(V);

the Group 5 transition metal-containing thin film forming precursor being tert-butylimidobis(tertbutylamido)mono(tert-butylalkoxo)Niobium(V);

the Group 5 transition metal-containing thin film forming precursor being tert-butylimidobis(di(trimethylsilyl)amido)mono(tert-butylalkoxo)Niobium(V);

the Group 5 transition metal-containing thin film forming precursor being tert-butylimidobis(dimethylamido)mono(diethylhydroxylamino)Niobium(V);

the Group 5 transition metal-containing thin film forming precursor being tert-butylimidobis(diethylamido)mono(iso-propylalkoxo)Tantalum(V);

the Group 5 transition metal-containing thin film forming precursor being tert-butylimidobis(diethylamido)mono(tert-butylalkoxo) Tantalum (V);

the Group 5 transition metal-containing thin film forming precursor being tert-butylimidobis(dimethylamido)mono(iso-propylalkoxo)Tantalum(V);

the Group 5 transition metal-containing thin film forming precursor being tert-butylimidobis(dimethylamido)mono(tert-butylalkoxo)Tantalum (V);

the Group 5 transition metal-containing thin film forming precursor being tert-amylimidobis(diethylamido)mono(iso-propylalkoxo)Tantalum (V);

the Group 5 transition metal-containing thin film forming precursor being tert-amylimidobis(diethylamido)mono(tert-butylalkoxo)Tantalum (V);

the Group 5 transition metal-containing thin film forming precursor being tert-amylimidobis(dimethylamido)mono(iso-propylalkoxo)Tantalum (V);

the Group 5 transition metal-containing thin film forming precursor being tert-amylimidobis(dimethylamido)mono(tert-butylalkoxo)Tantalum (V);

the Group 5 transition metal-containing thin film forming precursor being tert-butylimidobis(tertbutylamido)mono(tert-butylalkoxo)Tantalum(V);

the Group 5 transition metal-containing thin film forming precursor being tert-butylimidobis(di(trimethylsilyl)amido)mono(tert-butylalkoxo)Tantalum(V);

the Group 5 transition metal-containing thin film forming precursor being tert-butylimidobis(dimethylamido)mono(diethylhydroxylamino)Tantalum(V);

the Group 5 transition metal-containing thin film forming precursor being tert-butylimidomono(diethylamido)bis(iso-propylalkoxo)Vanadium(V);

the Group 5 transition metal-containing thin film forming precursor being tert-butylimidomono(diethylamido)bis(tert-butylalkoxo)Vanadium (V);

the Group 5 transition metal-containing thin film forming precursor being tert-butylimidomono(dimethylamido)bis(iso-propylalkoxo) Vanadium (V);

the Group 5 transition metal-containing thin film forming precursor being tert-butylimidomono(dimethylamido)bis(tert-butylalkoxo) Vanadium (V);

the Group 5 transition metal-containing thin film forming precursor being tert-amylimidomono(diethylamido)bis(iso-propylalkoxo) Vanadium (V);

the Group 5 transition metal-containing thin film forming precursor being tert-amylimidomono(diethylamido)bis(tert-butylalkoxo) Vanadium (V);

the Group 5 transition metal-containing thin film forming precursor being tert-amylimidomono(dimethylamido)bis(iso-propylalkoxo) Vanadium (V);

the Group 5 transition metal-containing thin film forming precursor being tert-amylimidomono(dimethylamido)bis(tert-butylalkoxo) Vanadium (V);

the Group 5 transition metal-containing thin film forming precursor being tert-butylimidomono(tert-butylamido)bis(tert-butylalkoxo)Vanadium(V);

the Group 5 transition metal-containing thin film forming precursor being tert-butylimidomono(di(trimethylsilyl)amido)bis(tert-butylalkoxo)Vanadium(V);

the Group 5 transition metal-containing thin film forming precursor being tert-butylimidomono(dimethylamido)bis(diethylhydroxylamino)Vanadium(V);

the Group 5 transition metal-containing thin film forming precursor being tert-butylimidomono(diethylamido)bis(iso-propylalkoxo)Niobium(V);

the Group 5 transition metal-containing thin film forming precursor being tert-butylimidomono(diethylamido)bis(tert-butylalkoxo) Niobium(V);

the Group 5 transition metal-containing thin film forming precursor being tert-butylimidomono(dimethylamido)bis(iso-propylalkoxo)Niobium(V);

the Group 5 transition metal-containing thin film forming precursor being tert-butylimidomono(dimethylamido)bis(tert-butylalkoxo)Niobium(V);

the Group 5 transition metal-containing thin film forming precursor being tert-amylimidomono(diethylamido)bis(iso-propylalkoxo)Niobium(V);

the Group 5 transition metal-containing thin film forming precursor being tert-amylimidomono(diethylamido)bis(tert-butylalkoxo)Niobium(V);

the Group 5 transition metal-containing thin film forming precursor being tert-amylimidomono(dimethylamido)bis(iso-propylalkoxo)Niobium(V);

the Group 5 transition metal-containing thin film forming precursor being tert-amylimidomono(dimethylamido)bis(tert-butylalkoxo)Niobium(V);

the Group 5 transition metal-containing thin film forming precursor being tert-butylimidomono(tert-butylamido)bis(tert-butylalkoxo)Niobium(V);

the Group 5 transition metal-containing thin film forming precursor being tert-butylimidomono(di(trimethylsilyl)amido)bis(tert-butylalkoxo)Niobium(V);

the Group 5 transition metal-containing thin film forming precursor being tert-butylimidomono(dimethylamido)bis(diethylhydroxylamino)Niobium(V);

the Group 5 transition metal-containing thin film forming precursor being tert-butylimidomono(diethylamido)bis(iso-propylalkoxo)Tantalum(V);

the Group 5 transition metal-containing thin film forming precursor being tert-butylimidomono(diethylamido)bis(tert-butylalkoxo)Tantalum(V);

the Group 5 transition metal-containing thin film forming precursor being tert-butylimidomono(dimethylamido)bis(iso-propylalkoxo)Tantalum(V);

the Group 5 transition metal-containing thin film forming precursor being tert-butylimidomono(dimethylamido)bis(tert-butylalkoxo)Tantalum(V);

the Group 5 transition metal-containing thin film forming precursor being tert-amylimidomono(diethylamido)bis(iso-propylalkoxo)Tantalum(V);

the Group 5 transition metal-containing thin film forming precursor being tert-amylimidomono(diethylamido)bis(tert-butylalkoxo)Tantalum(V);

the Group 5 transition metal-containing thin film forming precursor being tert-amylimidomono(dimethylamido)bis(iso-propylalkoxo)Tantalum(V);

the Group 5 transition metal-containing thin film forming precursor being tert-amylimidomono(dimethylamido)bis(tert-butylalkoxo)Tantalum(V);

the Group 5 transition metal-containing thin film forming precursor being tert-butylimidomono(tert-butylamido)bis(tert-butylalkoxo)Tantalum(V);

the Group 5 transition metal-containing thin film forming precursor being tert-butylimidomono(di(trimethylsilyl)amido)bis(tert-butylalkoxo)Tantalum(V); and the Group 5 transition metal-containing thin film forming precursor being tert-butylimidomono(dimethylamido)bis(diethylhydroxylamino)Tantalum(V).

Also disclosed are processes for the deposition of Group 5 transition metal-containing films on one or more substrates. At least one Group 5 transition metal-containing thin film forming precursor disclosed above is introduced into a reactor having at least one substrate disposed therein. At least part of the Group 5 transition metal-containing thin film forming precursor is deposited onto the at least one substrate to form the Group 5 transition metal-containing film.

The disclosed processes may further include one or more of the following aspects:

introducing at least one reactant into the reactor;
the reactant being plasma-treated;
the reactant being remote plasma-treated;
the reactant not being plasma-treated;
the reactant being selected from the group consisting of $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
the reactant being $H_2$;
the reactant being $NH_3$;
the reactant being selected from the group consisting of: $O_2$, $O_3$, $H_2O$, $H_2O_2$, NO, $N_2O$, $NO_2$, oxygen radicals thereof, and mixtures thereof;
the reactant being $H_2O$;
the reactant being plasma treated $O_2$;
the reactant being $O_3$;
the Group 5 transition metal-containing compound and the reactant being introduced into the reactor simultaneously;
the reactor being configured for chemical vapor deposition;
the reactor being configured for plasma enhanced chemical vapor deposition;
the Group 5 transition metal-containing compound and the reactant being introduced into the chamber sequentially;
the reactor being configured for atomic layer deposition;
the reactor being configured for plasma enhanced atomic layer deposition;
the reactor being configured for spatial atomic layer deposition;
the Group 5 transition metal-containing film being a pure Group 5 transition metal thin film;
the Group 5 transition metal-containing film being a Group 5 transition metal silicide ($M_kSi_l$, wherein M is the Group 5 transition metal and each of k and l is an integer which inclusively range from 1 to 6);
the Group 5 transition metal-containing film being a Group 5 transition metal oxide ($M_nO_m$, wherein M is the Group 5 transition metal and each of n and m is an integer which inclusively range from 1 to 6);
the Group 5 transition metal-containing film being $Nb_2O_5$;
the Group 5 transition metal-containing film being $Ta_2O_5$;
the Group 5 transition metal-containing film being a Group 5 transition metal nitride ($M_oN_p$, wherein M is the Group 5 transition metal and each of o and p is an integer which inclusively range from 1 to 6);
the substrate being zirconium oxide ($ZrO_2$); and
the substrate being titanium nitride (TiN).

NOTATION AND NOMENCLATURE

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; the abbreviation, "iPr," refers to an isopropyl group; the abbreviation "Bu" refers to butyl; the abbreviation "tBu" refers to tert-butyl; the abbreviation "sBu" refers to sec-butyl; the abbreviation "Cp" refers to cyclopentadienyl; the abbreviation "Cp*" refers to pentamethylcyclopentadienyl; the abbreviation "op" refers to (open)pentadienyl.

The standard abbreviations of the elements from the periodic table of elements are used herein. It should be understood that elements may be referred to by these abbreviations (e.g., Mn refers to manganese, Si refers to silicon, C refers to carbon, etc.).

BRIEF DESCRIPTION OF THE FIGURES

For a further understanding of the nature and objects of the present invention, reference should be made to the following detailed description, taken in conjunction with the accompanying figure wherein.

DESCRIPTION OF PREFERRED EMBODIMENTS

Disclosed are Group 5 transition metal-containing compounds having one of the following formulae:

Formula I

Formula II wherein M is selected from Group 5 transition metals consisting of V, Nb, and Ta and each R$^1$, R$^2$, R$^3$, R$^4$, R$^5$, and R$^6$ is independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. In Formula I, R$^3$ and R$^4$ may be identical or different. In Formula II, R$^4$ and R$^5$ may be identical or different. In Formula I, R$^3$, R$^4$, R$^5$ and R$^6$ may be identical or different.

Preferably R$^1$ is tBu or tert-amyl because bulky tertiary alkyl groups may help stabilize the imido group. Preferably R$^2$ in Formula I and R$^2$ and R$^3$ in Formula II is iPr or tBu because bulky alkyl groups may prevent dimerisation of the structure. Preferably R$^3$, R$^4$, R$^5$, and R$^6$ in Formula I or R$^4$ and R$^5$ in Formula II are Me or Et because smaller alkyl groups may lower the vapor pressure of the metal-containing compound.

Exemplary Group 5 transition metal-containing compounds include but are not limited to: tert-butylimidobis(diethylamido)mono(isopropylalkoxo)Vanadium (V); tert-butylimidobis(diethylamido)mono(tert-butylalkoxo) Vanadium (V); tert-butylimidobis(dimethylamido)mono(iso-propylalkoxo)Vanadium (V); tert-butylimidobis(dimethylamido)mono(tert-butylalkoxo)Vanadium (V); tert-amylimidobis(diethylamido)mono(iso-propylalkoxo) Vanadium (V); tert-amylimidobis(diethylamido)mono(tert-butylalkoxo)Vanadium (V); tert-amylimidobis(dimethylamido)mono(iso-propylalkoxo)Vanadium (V); tert-amylimidobis(dimethylamido)mono(tert-butylalkoxo) Vanadium (V); tert-butylimidobis(tertbutylamido)mono(tert-butylalkoxo) Vanadium(V); tert-butylimidobis(di(trimethylsilyl)amido)mono(tert-butylalkoxo) Vandadium(V); tert-butylimidobis(dimethylamido)mono(diethylhydroxylamino)Vanadium(V); tert-butylimidobis(diethylamido) mono(iso-propylalkoxo)Niobium(V); tert-butylimidobis(diethylamido)mono(tert-butylalkoxo)Niobium(V); tert-butylimidobis(dimethylamido)mono(iso-propylalkoxo) Niobium(V); tert-butylimidobis(dimethylamido)mono(tert-butylalkoxo)Niobium(V); tert-amylimidobis(diethylamido) mono(iso-propylalkoxo)Niobium(V); tert-amylimidobis (diethylamido)mono(tert-butylalkoxo)Niobium(V); tert-amylimidobis(dimethylamido)mono(iso-propylalkoxo) Niobium(V); tert-amylimidobis(dimethylamido)mono(tert-butylalkoxo)Niobium(V); tert-butylimidobis(tertbutylamido)mono(tert-butylalkoxo)Niobium(V); tert-butylimidobis(di(trimethylsilyl)amido)mono(tert-butylalkoxo) Niobium(V); tert-butylimidobis(dimethylamido)mono(diethylhydroxylamino) Niobium(V); tert-butylimidobis(diethylamido)mono(iso-propylalkoxo) Tantalum(V); tert-butylimidobis(diethylamido)mono(tert-butylalkoxo) Tantalum (V); tert-butylimidobis(dimethylamido)mono(iso-propylalkoxo) Tantalum(V); tert-butylimidobis(dimethylamido)mono(tert-butylalkoxo) Tantalum (V); tert-amylimidobis(diethylamido)mono(iso-propylalkoxo)Tantalum (V); tert-amylimidobis (diethylamido)mono(tert-butylalkoxo)Tantalum (V); tert-amylimidobis(dimethylamido)mono(iso-propylalkoxo) Tantalum (V); tert-amylimidobis(dimethylamido)mono(tert-butylalkoxo)Tantalum (V); tert-butylimidobis(tertbutylamido)mono(tert-butylalkoxo) Tantalum(V); tert-butylimidobis(di(trimethylsilyl)amido)mono(tert-butylalkoxo) Tantalum(V); tert-butylimidobis(dimethylamido)mono(diethylhydroxylamino) Tantalum (V); tert-butylimidomono(diethylamido)bis(iso-propylalkoxo) Vanadium(V); tert-butylimidomono(diethylamido)bis(tert-butylalkoxo) Vanadium (V); tert-butylimidomono(dimethylamido)bis(iso-propylalkoxo) Vanadium (V); tert-butylimidomono(dimethylamido)bis (tert-butylalkoxo) Vanadium (V); tert-amylimidomono(diethylamido)bis(iso-propylalkoxo) Vanadium (V); tert-amylimidomono(diethylamido)bis(tert-butylalkoxo) Vanadium (V); tert-amylimidomono(dimethylamido)bis(iso-propylalkoxo) Vanadium (V); tert-amylimidomono(dimethylamido) bis(tert-butylalkoxo) Vanadium (V); tert-butylimidomono (tert-butylamido)bis(tert-butylalkoxo) Vanadium(V); tert-butylimidomono(di(trimethylsilyl)amido)bis(tert-butylalkoxo) Vanadium(V); tert-butylimidomono (dimethylamido) bis(diethylhydroxylamino) Vanadium(V); tert-butylimidomono(diethylamido) bis(iso-propylalkoxo) Niobium(V); tert-butylimidomono(diethylamido) bis(tert-butylalkoxo)Niobium(V); tert-butylimidomono(dimethylamido) bis(iso-propylalkoxo)Niobium(V); tert-butylimidomono(dimethylamido) bis(tert-butylalkoxo) Niobium(V); tert-amylimidomono(diethylamido)bis(iso-propylalkoxo)Niobium(V); tert-amylimidomono (diethylamido)bis(tert-butylalkoxo)Niobium(V); tert-amylimidomono(dimethylamido)bis(iso-propylalkoxo) Niobium(V); tert-amylimidomono(dimethylamido)bis(tert-butylalkoxo)Niobium(V); tert-butylimidomono(tert-butylamido)bis(tert-butylalkoxo) Niobium(V); tert-butylimidomono(di(trimethylsilyl)amido) bis(tert-butylalkoxo)Niobium(V); tert-butylimidomono (dimethylamido) bis(diethylhydroxylamino)Niobium(V); tert-butylimidomono(diethylamido) bis(iso-propylalkoxo) Tantalum(V); tert-butylimidomono(diethylamido) bis(tert-butylalkoxo)Tantalum(V); tert-butylimidomono(dimethylamido) bis(iso-propylalkoxo)Tantalum(V); tert-butylimidomono(dimethylamido) bis(tert-butylalkoxo) Tantalum(V); tert-amylimidomono(diethylamido)bis(iso-propylalkoxo)Tantalum(V); tert-amylimidomono (diethylamido)bis(tert-butylalkoxo)Tantalum(V); tert-amylimidomono(dimethylamido)bis(iso-propylalkoxo) Tantalum(V); tert-amylimidomono(dimethylamido)bis(tert-butylalkoxo) Tantalum(V); tert-butylimidomono(tert-butylamido)bis(tert-butylalkoxo) Tantalum(V); tert-butylimidomono(di(trimethylsilyl)amido) bis(tert-butylalkoxo) Tantalum(V); and tert-butylimidomono(dimethylamido) bis (diethylhydroxylamino) Tantalum(V).

Preferably, the Group 5 transition metal-containing compound is either tert-butylimidobis(diethylamido)mono(tert-butylalkoxo)Niobium(V) or tert-butylimidomono(diethylamido)bis(tert-butylalkoxo)Niobium(V), due to its excellent vaporization results in atmospheric thermogravimetric analysis, leaving a small amount of final residue.

The disclosed Group 5 transition metal-containing compounds may be synthesized by reacting the corresponding alcohols with the corresponding imidotrisamido Group 5 transition metal in a suitable solvent, such as THF and ether at low temperature. An exemplary synthesis method containing further details is provided in the Examples that follow.

Also disclosed are methods for forming a Group 5 transition metal-containing layer on a substrate using a vapor deposition process. The method may be useful in the manufacture of semiconductor, photovoltaic, LCD-TFT, or flat panel type devices. The disclosed Group 5 transition metal-containing compounds may be used to deposit thin Group 5 transition metal-containing films using any deposition methods known to those of skill in the art. Examples of suitable deposition methods include without limitation, conventional chemical vapor deposition (CVD), atomic layer deposition (ALD), or other types of depositions that are related to vapor coating such as a plasma enhanced CVD (PECVD), plasma enhanced ALD (PEALD), pulsed CVD (PCVD), low pressure CVD (LPCVD), sub-atmospheric CVD (SACVD) or atmospheric pressure CVD (APCVD), hot-wire CVD (HW-CVD, also known as cat-CVD, in which a hot wire serves as an energy source for the deposition process), spatial ALD, hot-wire ALD (HWALD), radicals incorporated deposition, and super critical fluid deposition or combinations thereof. The deposition method is preferably ALD, PE-ALD, or spatial ALD in order to provide suitable step coverage and film thickness control.

The disclosed Group 5 transition metal-containing compounds may be supplied either in neat form or in a blend with a suitable solvent, such as ethyl benzene, xylene, mesitylene, decane, dodecane. The disclosed compounds may be present in varying concentrations in the solvent.

One or more of the neat or blended Group 5 transition metal-containing compounds are introduced into a reactor in vapor form by conventional means, such as tubing and/or flow meters. The compound in vapor form may be produced by vaporizing the neat or blended compound solution through a conventional vaporization step such as direct vaporization, distillation, or by bubbling. The neat or blended compound may be fed in liquid state to a vaporizer where it is vaporized before it is introduced into the reactor. Alternatively, the neat or blended compound may be vaporized by passing a carrier gas into a container containing the compound or by bubbling the carrier gas into the compound. The carrier gas may include, but is not limited to, Ar, He, $N_2$, and mixtures thereof. Bubbling with a carrier gas may also remove any dissolved oxygen present in the neat or blended compound solution. The carrier gas and compound are then introduced into the reactor as a vapor.

If necessary, the container of disclosed compound may be heated to a temperature that permits the compound to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of compound vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the compounds to react and form the layers.

Generally, the reactor contains one or more substrates onto which the thin films will be deposited. The substrates may be any suitable substrate used in semiconductor, photovoltaic, flat panel, or LCD-TFT device manufacturing. Examples of suitable substrates include without limitation, silicon substrates, silica substrates, silicon nitride substrates, silicon oxy nitride substrates, tungsten substrates, or combinations thereof. Plastic substrates, such as poly(3,4-ethylenedioxythiophene)poly (styrenesulfonte) [PEDOT:PSS], may also be used. Additionally, substrates comprising tungsten or noble metals (e.g. platinum, palladium, rhodium, or gold) may be used. The substrate may also have one or more layers of differing materials already deposited upon it from a previous manufacturing step. For example, a $Nb_2O_5$ film may be deposited onto a $ZrO_2$ substrate. In subsequent processing, a $ZrO_2$ layer may be deposited on the $Nb_2O_5$ layer, forming a $ZrO_2/Nb_2O_5/ZrO_2$ DRAM capacitor. In another example, a $Ta_2O_5$ layer may be deposited between two TiN layers, forming a BEOL (back end of the line) TiN/$Ta_2O_5$/TiN MIM capacitor.

The temperature and the pressure within the reactor are held at conditions suitable for ALD or CVD depositions. In other words, after introduction of the vaporized compound into the chamber, conditions within the chamber are such that at least part of the vaporized compound is deposited onto the substrate to form a Group 5 transition metal-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 350° C. One of ordinary skill in the art will recognize that "at least part of the vaporized compound is deposited" means that some or all of the compound reacts with or adheres to the substrate.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 350° C. Alternatively, when a thermal process is performed, the deposition temperature may range from approximately 200° C. to approximately 500° C.

In addition to the disclosed compound, a reactant may also be introduced into the reactor. The reactant may be an oxidizing gas such as one of $O_2$, $O_3$, $H_2O$, $H_2O_2$, NO, $N_2O$, $NO_2$, oxygen containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as O. or OH., and mixtures thereof.

Alternatively, the reactant may be a reducing gas such as one of $H_2$, $H_2CO$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof. Preferably, the reducing as is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by a plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Group 5 transition metal-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 3 Torr to approximately 10 Torr, the reactant $O_2$ may be decomposed into two O. radicals. Preferably, the remote plasma may be generated with a power ranging from about 1 kW to about 10 kW, more preferably from about 2.5 kW to about 7.5 kW.

The vapor deposition conditions within the chamber allow the disclosed compound and the reactant to react and form a Group 5 transition metal-containing film on the substrate. In some embodiments, Applicants believe that plasma-treating the reactant may provide the reactant with the energy needed to react with the disclosed compound.

Depending on what type of film is desired to be deposited, an additional precursor compound may be introduced into the reactor. The precursor may be used to provide additional elements to the Group 5 transition metal-containing film. The additional elements may include copper, praseodymium, manganese, ruthenium, titanium, tantalum, bismuth, zirconium, hafnium, lead, vanadium, niobium, tantalum, magnesium, aluminum, lanthanum, or mixtures of these. When an additional precursor compound is utilized, the resultant film deposited on the substrate may contain Group 5 transition metal in combination with at least one additional element.

The Group 5 transition metal-containing compounds and reactants may be introduced into the reactor either simultaneously (chemical vapor deposition), sequentially (atomic layer deposition) or different combinations thereof. The reactor may be purged with an inert gas between the introduction of the compound and the introduction of the reactant. Alternatively, the reactant and the compound may be mixed together to form a reactant/compound mixture, and then introduced to the reactor in mixture form. Another example is to introduce the reactant continuously and to introduce the at least one Group 5 transition metal-containing compound by pulse (pulsed chemical vapor deposition).

The vaporized compound and the reactant may be pulsed sequentially or simultaneously (e.g. pulsed CVD) into the reactor. Each pulse of compound may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds. In another alternative, the vaporized compound and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties.

Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed Group 5 transition metal-containing compound and a reactant are simultaneously introduced into the reactor. The two react to form the resulting Group 5 transition metal-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed Group 5 transition metal-containing compound is introduced into the reactor, where it is contacted with a suitable substrate. Excess compound may then be removed from the reactor by purging and/or evacuating the reactor. A desired gas (for example, $H_2$) is introduced into the reactor where it reacts with the absorbed compound in a self-limiting manner. Any excess reducing gas is removed from the reactor by purging and/or evacuating the reactor. If the desired film is a Group 5 transition metal film, this two-step process may provide the desired film thickness or may be repeated until a film having the necessary thickness has been obtained.

Alternatively, if the desired film contains Group 5 transition metal and a second element, the two-step process above may be followed by introduction of the vapor of an additional precursor compound into the reactor. The additional precursor compound will be selected based on the nature of the Group 5 transition metal film being deposited. After introduction into the reactor, the additional precursor compound is contacted with the substrate. Any excess precursor compound is removed from the reactor by purging and/or evacuating the reactor. Once again, a desired gas may be introduced into the reactor to react with the precursor compound. Excess gas is removed from the reactor by purging and/or evacuating the reactor. If a desired film thickness has been achieved, the process may be terminated. However, if a thicker film is desired, the entire four-step process may be repeated. By alternating the provision of the Group 5 transition metal-containing compound, additional precursor compound, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

In another non-limiting exemplary ALD type process, the vapor phase of a Zr-containing precursor, for example one of the $ZrCp(NR_2)_3$ precursors, preferably $ZrCp(NMe_2)_3$, disclosed in PCT Publication No. WO2007/141059, is introduced into the reactor, where it is contacted with a suitable substrate. Excess Zr-containing precursor may then be removed from the reactor by purging and/or evacuating the reactor. A desired gas (for example, $O_3$) is introduced into the reactor where it reacts with the absorbed Zr-containing precursor in a self-limiting manner to form a $ZrO_2$ film. Any excess oxidizing gas is removed from the reactor by purging and/or evacuating the reactor. These two steps may be repeated until the $ZrO_2$ film obtains a desired thickness.

The vapor phase of one of the disclosed Nb-containing precursor, for example tert-butylimidobis(diethylamido) mono(tert-butylalkoxo)Niobium(V) or tert-butylimidomono (diethylamido)bis(tert-butylalkoxo)Niobium(V), is introduced into the reactor, where it is contacted with the $ZrO_2$ substrate. Excess Nb-containing precursor may then be removed from the reactor by purging and/or evacuating the reactor. A desired gas (for example, $O_3$) is introduced into the reactor where it reacts with the absorbed Nb-containing precursor in a self-limiting manner to form a $Nb_2O_5$ film. Any excess oxidizing gas is removed from the reactor by purging and/or evacuating the reactor. These two steps may be repeated until the $Nb_2O_5$ film obtains a desired thickness.

Finally, the vapor phase of a Zr-containing precursor, which may be the same or different from the previous Zr-containing precursor, is introduced into the reactor, where it is contacted with the $Nb_2O_5/ZrO_2$ substrate. Excess Zr-containing precursor may then be removed from the reactor by purging and/or evacuating the reactor. A desired gas (for example, $O_3$) is introduced into the reactor where it reacts with the absorbed Zr-containing precursor in a self-limiting manner to form a $ZrO_2$ film. Any excess oxidizing gas is removed from the reactor by purging and/or evacuating the reactor. These two steps may be repeated until the $ZrO_2$ film obtains a desired thickness.

The resulting $ZrO_2/Nb_2O_5/ZrO_2$ layer may be used in DRAM capacitors.

In another non-limiting exemplary ALD type process, Tantalum or Niobium oxide thin films may be used as an insulator for the fabrication of Metal-Insulator-Metal capacitors (MIM cap) in the Back-End-of-Line level where the temperature budget is limited. In order to keep a low the thermal budget, the plasma enhanced process is typically used. In such a MIM cap structure, the substrate might be without limitation Titanium Nitride (TiN). In a typical example the Tantalum or Niobium oxide thin films will be deposited on TIN or partially oxidized TiN (TiON). In a typical process, the oxidant gas, such as oxygen, will continuously flow into the reactor. The vapor phase of one of the disclosed Nb- or Ta-containing precursors, for example tert-butylimidobis(diethylamido)mono(tert-butylalkoxo) Niobium(V) or tert-butylimidomono(diethylamido)bis(tert-butylalkoxo) Niobium(V), or tert-butylimidobis(diethylamido)mono(tert-butylalkoxo) Tantalum(V) or tert-butylimidomono(diethylamido)bis(tert-butylalkoxo) Tantalum(V), is pulsed into the reactor. Plasma activation occurs alternate to the precursor pulse cycle. In other words, the cycle would be continuous oxidant introduction, with alternating precursor and plasma pulses. The process does not include the typical ALD purge cycle, helping to decrease the cycle time. The resulting $TIN-Ta(Nb)_2O_5$-TIN stack may be used in BEOL MIM capacitors.

The Group 5 transition metal-containing films resulting from the processes discussed above may include a pure Group 5 transition metal (M=V, Nb, Ta), Group 5 transition metal silicide ($M_kSi_l$), Group 5 transition metal oxide ($M_nO_m$), or Group 5 transition metal nitride ($M_oN_p$) film wherein k, l, m, n, o and p are integers which inclusively range from 1 to 6. One of ordinary skill in the art will recognize that by judicial selection of the appropriate disclosed compound, optional precursor compounds, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Group 5 transition metal-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Group 5 transition metal-containing film. This in turn tends to improve the resistivity of the film.

In another alternative, the disclosed Group 5 transition metal-containing compounds may be used as doping or implantation agents. Part of the disclosed Group 5 transition metal-containing compound may be deposited on top of the film to be doped, such as an indium oxide ($In_2O_3$) film, vanadium dioxide ($VO_2$) film, a titanium oxide film, a copper oxide film, or a tin dioxide ($SnO_2$) film. The Group 5 transition metal then diffuses into the film during an annealing step to form the Group 5 transition metal-doped films {(V)$In_2O_3$, (Nb)$VO_2$, (Ta)TiO, (V)CuO, or (Nb)$SnO_2$}. See, e.g., US2008/0241575 to Lavoie et al., the doping method of which is incorporated herein by reference in its entirety. Alternatively, high energy ion implantation using a variable energy radio frequency quadrupole implanter may be used to dope the Group 5 transition metal of the disclosed compounds into a film. See, e.g., Kensuke et al., JVSTA 16(2) March/April 1998, the implantation method of which is incorporated herein by reference in its entirety. In another alternative, plasma doping, pulsed plasma doping or plasma immersion ion implantation may be performed using the disclosed Group 5 transition metal-containing compounds. See, e.g., Felch et al., Plasma doping for the fabrication of ultra-shallow junctions Surface Coatings Technology, 156 (1-3) 2002, pp. 229-236, the doping method of which is incorporated herein by reference in its entirety.

EXAMPLES

The following examples illustrate experiments performed in conjunction with the disclosure herein. The examples are not intended to be all inclusive and are not intended to limit the scope of disclosure described herein.

Example 1: tert-BuN=Nb(NEt$_2$)$_2$(OtBu) Synthesis

To a solution of tert-BuN=Nb(NEt$_2$)$_3$ (2 g, 5.26 mmol) in ca. 20 mL of tetrahydrofuran (THF) at −78° C., was added a solution of tBuOH (0.38 g, 5.26 mmol) in THF dropwise. The mixture was slowly warmed to room temperature and stirred overnight. Solvent was then removed under vacuum to give a yellow liquid. The material was purified by distillation at 120° C. @ 100 mTorr (bp~55-65° C.) to give 1.12 g (56%) of a colorless oil.

Figure 1:
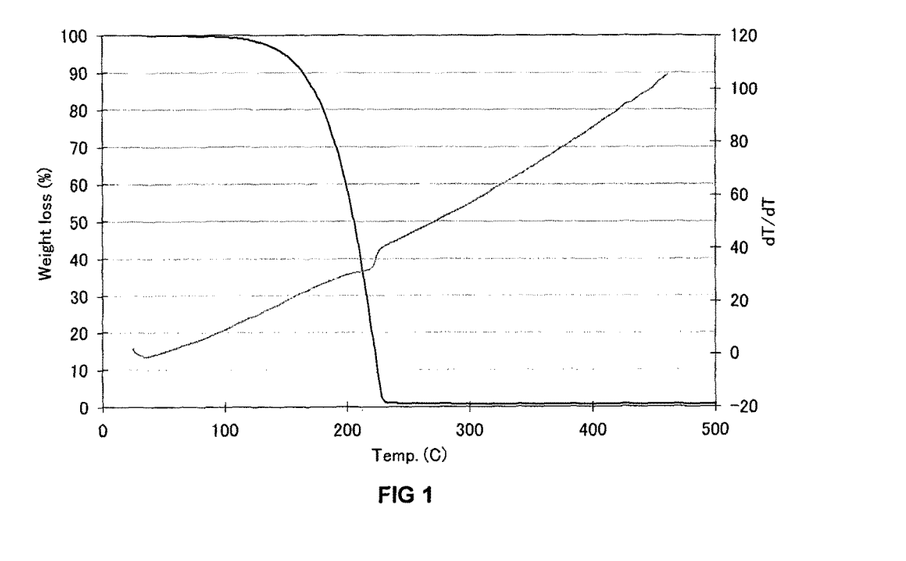
FIG. 1 is a ThermoGravimetric Analysis (TGA)/Differential Thermal Analysis (DTA) graph demonstrating the percentage of weight loss (TGA) or the differential temperature (DTA) with increasing temperature of tert-BuN=Nb(NEt$_2$)$_2$(OtBu)
Figure 3:
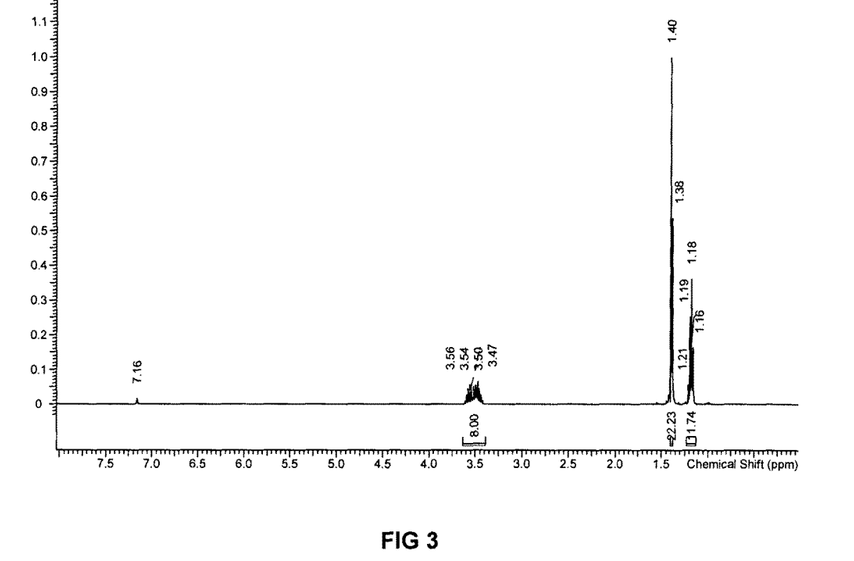
FIG. 3 is a $^1$HNMR spectrum of tert-BuN=Nb(NEt$_2$)$_2$(OtBu)

The oil left a <1% residual mass during TGA analysis measured at a temperature rising rate of 10° C./min in an atmosphere which flows nitrogen at 200 mL/min. These results are depicted in FIG. 1, which is a TGA graph demonstrating the percentage of weight loss with temperature change. The NMR1H spectrum is provided in FIG. 3.

NMR1H (δ, ppm, C6D6): 3.52 (m, 8H), 1.40 (s, 9H), 1.38 (s, 9H), 1.18 (m, 12H)

Example 2: tert-BuN=Nb(NEt$_2$)(OtBu)$_2$ Synthesis

To a solution of tert-BuN=Nb(NEt$_2$)$_3$ (2 g, 5.26 mmol) in ca. 20 mL of THF at −78° C., was added a solution of tBuOH (0.78 g, 10.52 mmol) dropwise. The mixture was slowly warmed to room temperature and stirred overnight. Solvent was then removed under vacuum to give a yellow liquid. The material was purified by distillation at 150° C. @ 100 mTorr (bp~70-80° C.) to give 1.43 g (71%) of a colorless oil.

Figure 2:
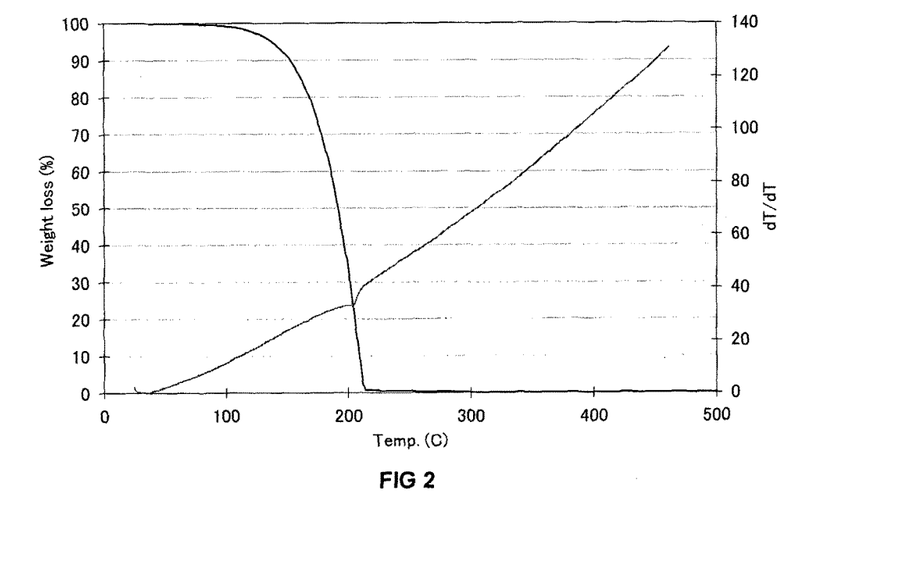
FIG. 2 is a TGA/DTA graph demonstrating the percentage of weight loss (TGA) or the differential temperature (DTA) with increasing temperature of tert-BuN=Nb(NEt$_2$)(OtBu)$_2$.
Figure 4:
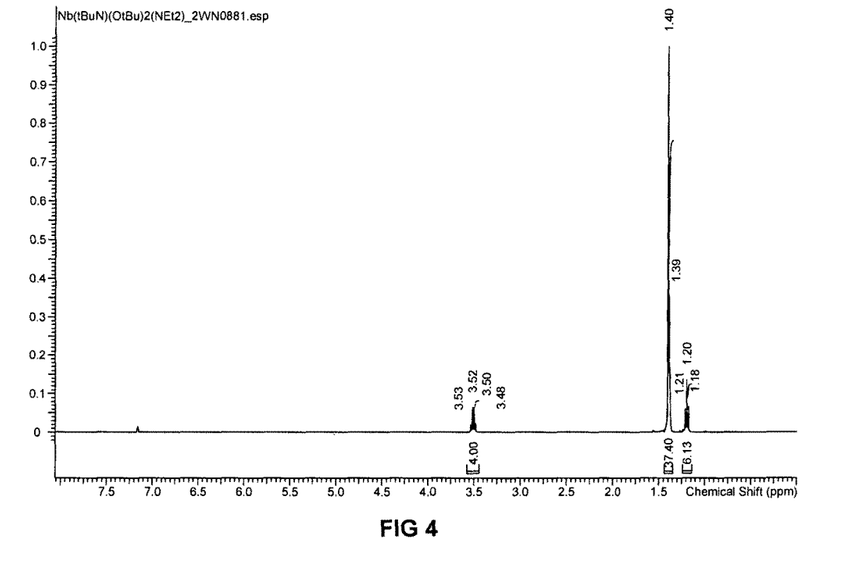
FIG. 4 is a $^1$HNMR spectrum of tert-BuN=Nb(NEt$_2$)(OtBu)$_2$.

The oil left a <1% residual mass during TGA analysis measured at a temperature rising rate of 10° C./min in an atmosphere which flows nitrogen at 200 mL/min. These results are depicted in FIG. 2, which is a TGA graph demonstrating the percentage of weight loss with temperature change. The NMR1H spectrum is provided in FIG. 4.

NMR1H (δ, ppm, C6D6): 3.52 (m, 4H), 1.40 (s, 18H), 1.39 (s, 9H), 1.20 (m, 6H)

Example 3: ALD of Group 5 Transition Metal

Figure 5:
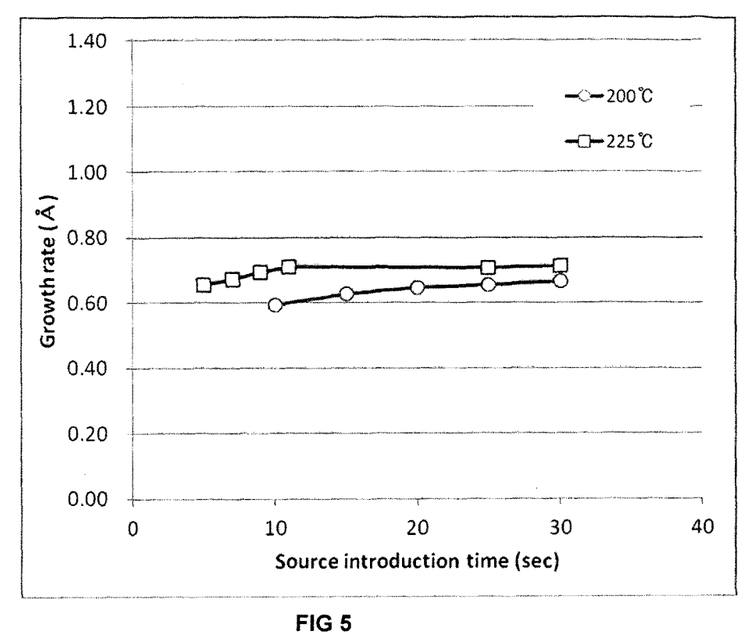
FIG. 5 is graph illustrating Atomic Layer Deposition saturation curves showing the growth rate in angstroms/cycle of the Nb$_2$O$_5$ film deposited in Example 3 versus source introduction time in seconds at 200° C. and 225° C.
Figure 6:
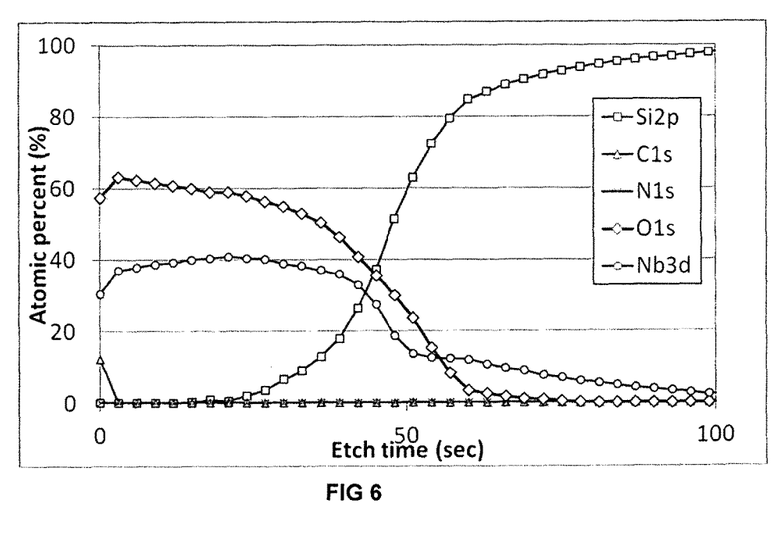
FIG. 6 is a X-ray Photoelectron Spectroscopy (XPS) graph showing the atomic percentage of Si, C, N, O and Nb contained in the Nb$_2$O$_5$ film deposited in Example 3 versus etch time in seconds.
Figure 7:
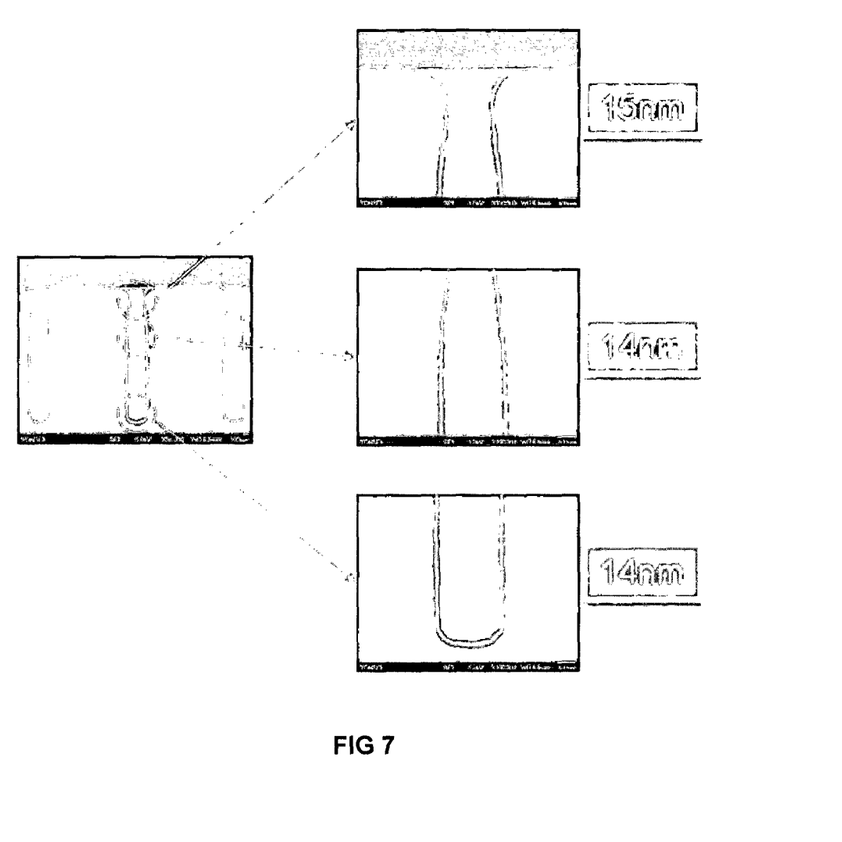
FIG. 7 are scanning electron microscope photographs of the Nb$_2$O$_5$ film deposited on a patterned wafer with trenches having an aspect ratio of 10:1.

ALD tests were performed using the tert-BuN=Nb(NEt$_2$)$_2$(OtBu) prepared in Example 1, placed in a vessel heated to 80° C. Typical ALD conditions were used with a reactor pressure fixed at 0.5 Torr. ALD behavior with complete surface saturation and reaction was observed at 200° C. and 225° C. on pure silicon wafers with growth rates of approximately 0.7 Å/cycle, as shown in FIG. 5. Carbon and nitrogen contamination were below the detection limit (i.e., less than 1% atomic), as displayed in FIG. 6. Excellent step coverage was obtained on a 10:1 aspect ratio patterned wafer (93% without optimization), as shown in FIG. 7.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

The invention claimed is:

1. A Group 5 transition metal-containing thin film forming precursor having one of the following formulae:

wherein the Group 5 transition metal-containing thin film forming precursor is tert-butylimidobis(diethylamido)mono (tert-butylalkoxo)Niobium(V) or tert-butylimidomono(diethylamido)bis(tert-butylalkoxo)Niobium(V).

2. The Group 5 transition metal-containing thin film forming precursor of claim 1, wherein the Group 5 transition metal-containing thin film forming precursor is tert-butylimidobis(diethylamido)mono(tert-butylalkoxo)Niobium (V).

3. The Group 5 transition metal-containing thin film forming precursor of claim 1, wherein the Group 5 transition metal-containing thin film forming precursor is tert-butylimidomono(diethylamido)bis(tert-butylalkoxo)Niobium (V).

4. A process for the deposition of a Group 5 transition metal-containing film on a substrate, comprising the steps of: introducing the vapor of the Group 5 transition metal-containing thin film forming precursor into a reactor having a substrate disposed therein and depositing at least part of the Group 5 transition metal-containing compound onto the substrate, the Group 5 transition metal-containing thin film forming precursor having one of the following formulae:

Formula I

Formula II wherein the Group 5 transition metal-containing thin film forming precursor is tert-butylimidobis(diethylamido)mono (tert-butylalkoxo)Niobium(V) or tert-butylimidomono(diethylamido)bis(tert-butylalkoxo)Niobium(V).

5. The process of claim 4, further comprising introducing at least one reactant into the reactor.

6. The process of claim 5, wherein the reactant is selected from the group consisting of $H_2$, $H_2CO$ $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof.

7. The process of claim 5, wherein the reactant is selected from the group consisting of: $O_2$, $O_3$, $H_2O$, $H_2O_2$ NO, $N_2O$, $NO_2$, oxygen radicals thereof, and mixtures thereof.

8. The process of claim 5, wherein the Group 5 transition metal-containing thin film forming precursor and the reactant are introduced into the reactor simultaneously and the reactor is configured for chemical vapor deposition.

9. The process of claim 5, wherein the Group 5 transition metal-containing thin film forming precursor and the reactant are introduced into the reactor sequentially and the reactor is configured for atomic layer deposition.

10. The process of claim 5, wherein the substrate is zirconium oxide ($ZrO_2$).

11. The process of claim 5, wherein the Group 5 transition metal-containing thin film forming precursor is tert-butylimidobis(diethylamido)mono(tert-butylalkoxo)Niobium (V).

12. The process of claim 5, wherein the Group 5 transition metal-containing thin film forming precursor is tert-butylimidomono(diethylamido)bis(tert-butylalkoxo)Niobium (V).

* * * * *